(12) United States Patent
Yunoki et al.

(10) Patent No.: US 6,563,000 B1
(45) Date of Patent: May 13, 2003

(54) PROCESS FOR PRODUCING ACRYLIC ACID

(75) Inventors: Hiromi Yunoki, Himeji (JP); Michio Tanimoto, Himeji (JP); Daisuke Nakamura, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/576,024

(22) Filed: May 23, 2000

(30) Foreign Application Priority Data

May 27, 1999 (JP) .......................................... 11-147451

(51) Int. Cl.$^7$ .......................... C07C 51/16; B01J 23/00; B01J 23/70
(52) U.S. Cl. .................. 562/532; 562/532; 562/535; 562/546; 502/302; 502/309; 502/318; 502/321; 502/345; 502/350
(58) Field of Search ................................ 562/532, 535, 562/546; 502/306, 309, 318, 321, 345, 350, 353

(56) References Cited

U.S. PATENT DOCUMENTS

| | | | |
|---|---|---|---|
| 3,567,772 A | | 3/1971 | Yanagita et al. |
| 3,801,634 A | | 4/1974 | Krabetz et al. |
| 3,954,855 A | * | 5/1976 | Wada et al. |
| 4,837,360 A | * | 6/1989 | Kadowaki et al. |
| 5,206,431 A | | 4/1993 | Hashiba et al. |
| 5,719,318 A | * | 2/1998 | Kawajiri et al. |

FOREIGN PATENT DOCUMENTS

| | | |
|---|---|---|
| CA | 1045106 | 12/1978 |
| EP | 0792866 | 9/1997 |
| JP | 411775 B1 | 2/1966 |
| JP | 4426287 | 11/1969 |
| JP | 5025914 | 8/1975 |
| JP | 5330688 | 8/1978 |
| JP | 5754172 | 11/1982 |
| JP | 6338331 | 7/1988 |
| JP | 710802 | 1/1995 |
| JP | 9241209 | 9/1997 |

* cited by examiner

Primary Examiner—Johann Richter
Assistant Examiner—Elvis O. Price
(74) Attorney, Agent, or Firm—Sherman & Shalloway

(57) ABSTRACT

A process for producing acrylic acid through vapor-phase catalytic oxidation of acrolein or acrolein-containing gas with molecular oxygen or a molecular oxygen-containing gas using a catalyst-filled fixed bed shell-and-tube reactor is provided, which is characterized in that plural catalysts of different activity levels which are prepared by changing the kind and/or amount of alkaline metal(s) therein are filled in the reaction tubes in such an arrangement that the activity levels rise from the gas-inlet side toward the gas-outlet side of said tubes. According to this process, not only yield and productivity of acrylic acid are improved but also excessive heat, accumulation in the catalyst layer can be inhibited and catalysts degradation under heat is prevented, resulting in prolongation of catalyst life.

3 Claims, No Drawings

PROCESS FOR PRODUCING ACRYLIC ACID

TECHNICAL FIELD TO WHICH THE INVENTION BELONGS

This invention relates to a process for producing acrylic acid by vapor-phase catalytic oxidation of acrolein or an acrolein-containing gas with molecular oxygen or a molecular oxygen-containing gas, using a fixed bed shell-and-tube reactor.

CONVENTIONAL TECHNOLOGY

A large number of proposals have been made in the past concerning the catalysts to be used in the occasions of preparing acrylic acid through vapor-phase catalytic oxidation of acrolein or acrolein-containing gas. For example, Official Gazettes of Patent Publications, Sho 41 (1966)-1775B1 disclosed catalysts comprising molybdenum and vanadium; Sho 44 (1969)-26287B1 disclosed those comprising molybdenum, vanadium and aluminium; Sho 50 (1975)-25914B1, those comprising molybdenum and vanadium, which are prepared by a process characterized in that vanadyl oxalate is caused to be present at the time of the catalyst preparation; and Sho 57 (1982)-54172B1, those comprising molybdenum, vanadium, titanium and optionally at least an element selected from the group consisting of iron, copper, cobalt, chromium and manganese. Of these catalysts, some do attain considerably high level of acrylic acid yield from industrial standpoint, but industrial production of acrylic acid using these catalysts is still subject to a number of problems.

One of the problems is occurrence of localized abnormally high temperature zone (hot spot) in the catalyst layer. For example, in industrial scale production, productivity of the object product, i.e., acrylic acid, must be raised, and generally such means as increasing concentration of starting acrolein or space velocity are adopted to achieve this purpose. When such means is adopted, however, the reaction conditions come to be considerably restricted, because the involved vapor-phase catalytic reaction is extremely exothermic and under the heavy-load operative condition, the temperature at the hot spot rises with increase in the reaction amount of acrolein. In consequence, over-oxidation takes place to reduce the yield and accelerate thermal deterioration of the catalyst, in the worst case even causing run-away reaction.

For controlling formation of a hot spot or abnormal accumulation of heat at the hot spot, acrolein concentration in the starting material may be dropped or the space velocity may be decreased. However, such means lower the productivity and are economically disadvantageous. Also as another means diameter of reaction tubes may be made small to improve heat-removing efficiency, but such is subject to limitations incurred in industrial production and to the disadvantage of high reactor cost.

As to means for keeping hot spot temperature low, a number of proposals have been made besides those stated above. For example, Official Gazettes of Patent Publications, Sho 53 (1978) 30688B1 disclosed a method of diluting the catalyst layer at the gas-inlet side of the reactor with an inert substance; and Hei 7 (1995)-10802A1 proposed a method of sequentially increasing the carried ratio of catalytically active substance, from the gas-inlet side toward the gas-outlet side of the reactor. However, in the former method, it requires strenuous effort to uniformly mix the inert substance for dilution with catalyst, and it is not always possible to fill the mixture in the reaction tubes, maintaining the uniformly mixed state, which render the method still unsatisfactory. In the latter method, it is not necessarily easy per se to control the carried ratios of catalytically active substance. Furthermore, the catalysts useful therefor are limited to those carrier-supported type, i.e., to those in which catalytically active components are carried on inert carriers, and the catalytically active component by itself, as compression-molded or tabletted, cannot be used. A still further problem common between the two methods is that the gas-inlet side catalyst deteriorates faster than the catalyst at the gas-outlet side because the amount of the catalytically active substance at the gas-inlet side is less than that at the gas-outlet side, and in consequence continuation of the reaction over prolonged period while maintaining a high yield may become impossible.

Therefore, to control the heat accumulation at the hot spot is very important for industrial production of acrylic acid at high yields as well as for enabling stable operation over prolonged periods, inhibiting catalyst deterioration. It is of particular importance to prevent accumulation of heat at the hot spot where molybdenum-containing catalysts are used, because molybdenum component readily sublimes.

Accordingly, therefore, the object of present invention is to provide a means for solving this problem.

MEANS FOR SOLVING THE PROBLEM

We have made concentrative studies with the view to solve the above problem and discovered that the above object can be accomplished by filling the reaction tubes in a fixed bed shell-and-tube reactor to be used for the reaction with catalyst following a specific design, i.e., by using plural kinds of catalysts having different activity levels and filling the reaction tubes with them as arranged in such a manner that the catalytic activity should increase from the gas-inlet side of the reaction tubes toward the gas-outlet side. Thus the present invention is completed.

Thus, according to the present invention, a process for producing acrylic acid by vapor-phase catalytic oxidation of acrolein or an acrolein-containing gas with molecular oxygen or a molecular oxygen-containing gas using a catalyst-filled fixed bed shell-and-tube reactor is provided, which process is characterized by providing plural reaction zones in each reaction tube in said fixed bed shell-and-tube reactor, by dividing inside of each of said tubes in the axial direction thereof, and filling the plural reaction zones with plural catalysts of different activity levels in such a manner that the activity level rises from the gas-inlet side of each reaction tube toward the gas-outlet side thereof.

WORKING EMBODIMENT OF THE INVENTION

The starting material used in the present invention is acrolein or acrolein-containing gas. As such, acrolein-containing gas produced upon catalytic vapor-phase oxidation of propylene can be used as it is, or the acrolein isolated therefrom may be used upon optional addition of oxygen, steam and other gas(es).

The catalysts used in the present invention are complex oxides whose essential components are molybdenum and vanadium and which are expressed by the following general formula (1)

$$Mo_a V_b W_c Cu_d A_e Q_f R_g D_h O_i \qquad (I)$$

(wherein Mo is molybdenum; V is vanadium; W is tungsten; Cu is copper; A is at least an element selected from the group consisting of zirconium, titanium and cerium; Q is at least an element selected from a group consisting of magnesium, calcium, strontium and barium; R is at least an element selected from the group consisting of niobium, antimony, tin, tellurium, phosphorus, cobalt, nickel, chromium, manganese, zinc and bismuth; D is at least an element selected from alkali metals; and O is oxygen; and a, b, c, d, e, f, g, h and i represent atomic ratios of Mo, V, W, Cu, A, Q, R, D and O, respectively, in which where a is 12, $1 \leq b \leq 14$, $0 < c \leq 12$, $0 < d \leq 6$, $0 \leq e \leq 10$, $0 \leq f \leq 3$, $0 \leq g \leq 10$ and $0 \leq h \leq 5$, and i is a numerical value determined by degree of oxidation of each of the elements).

These catalysts can be prepared by any methods which are generally practiced for preparing this type of catalysts. Starting materials to be used for preparing those catalysts are subject to no critical limitation, and ammonium salts, nitrates, carbonates, sulfates, hydroxides, oxides and the like of those metal elements, which have been generally used are useful. Compounds each containing plural metal elements may also be used.

Plural catalysts which are represented by general formula (I) and have different activity levels can be easily prepared by varying kind(s) and/or amount(s) of the D group elements in said general formula (I). More specifically, by selecting at least an element from alkali metals (lithium, sodium, potassium, rubidium, cesium etc.) constituting the D group and/or varying the amount of the so selected element within the atomic ratio specified therefor in general formula (I), catalysts of different activity levels can be obtained.

The term, "activity" as herein used signifies conversion of the starting material.

The catalysts to fill the reaction zones according to the invention may be molded catalysts formed by molding the catalytic components into a predetermined shape; carrier-supported catalysts in which the catalytic components are carried on an optional inert carrier having a specific shape; or such molded catalyst may be used in combination with carrier-supported catalyst. While shape of the catalysts to fill the reaction zones may be same or different, it is normally preferred that a molded catalyst of identical shape or a carrier-supported catalyst of identical shape should be filled within a same reaction zone.

The shape of the oxidation catalyst is subject to no critical limitation, which may be spherical, columnar, (pelletized), ring-formed or amorphous. Obviously, when it is spherical, it is unnecessary to be true spheres but may be substantially spherical. Obviously, this statement also applies to columns and rings.

When carrier-supported type catalysts are used, the ratio of the catalytic component to the carrier (carried ratio) in the catalyst which is filled in each reaction zone may be same or different, while it is normally simpler for the catalyst-producing operations and advantageous for prolonging the catalyst life, to use a catalyst of same carried ratio. Kind of the carrier material itself is not critical, but any of those which are normally useful in preparing catalysts for acrylic acid production through vapor-phase oxidation of acrolein may be used. Specific examples of useful carriers include alumina silica, silica-alumina, titania, magnesia, silica-magnesia, silica-magnesia-alumina, silicon carbide, silicon nitride, zeolite and the like.

Heat-treating temperature (calcining temperature) in the course of catalyst preparation is not subject to any particular limitation. The heat-treating temperatures of the catalysts to be filled in each of the reaction zones may be same or different.

According to the invention, inside space of each reaction tube in fixed bed shell-and-tube reactor is radially divided along the axial direction of the tube to provide plural reaction zones, and those plural reaction zones are filled with plural catalysts of different activity levels as above-described in such a manner that the activity should increase sequentially from the gas-inlet side toward the gas-outlet side. That is, a catalyst of the lowest activity is disposed at the gas-inlet side and that of the highest activity, at the gas-outlet side. By the arrangement of plural catalysts of different activity levels heat accumulation at the hot spot can be inhibited and the object product can be obtained with high selectivity.

The more the number of the reaction zones, the easier the temperature distribution control in the catalyst layers. For industrial practice, however, around 2 to 3 reaction zones are sufficient to accomplish the intended effect. The dividing ratio between the reaction zones cannot be generally determined because the optimum ratio depends on the reaction conditions and the composition, shape and size, etc. of the catalysts filling each of the reaction zones in individual runs. The ratio, therefore, may be suitably selected to obtain the optimum activity and selectivity as a whole.

The vapor-phase catalytic oxidation reaction can be conducted by either ordinary one-pass method or by recycling, under the conditions generally adopted for this type of reaction.

According to the process of the present invention, particularly remarkable, excelling result over conventional processes can be achieved under heavy-load reaction conditions intended for raising productivity, for example, under higher concentration of the starting material and/or higher space velocity.

EFFECTS OF THE INVENTION

According to the invention, such favorable effects as:

(a) acrylic acid is obtained at high yield, (b) heat accumulation at hot spot can be effectively inhibited, (c) catalyst deterioration under heat is prevented to allow stable use of the catalyst over prolonged period, and (d) productivity can be largely increased because the process is capable of producing acrylic acid at high yield with stability under such heavy-load operation conditions as high concentration of starting material and/or high space velocity, are obtained by using plural specific molybdenum-vanadium-containing catalysts of different activity levels and filling them in the catalyst layer which is divided into plural zones, in such a manner that the activity should increase from the gas-inlet side toward the gas-outlet side.

The process of the present invention, therefore, is very advantageous for industrial production of acrylic acid.

EXAMPLES

Hereinafter the present invention is explained more specifically referring to working Examples, it being understood that the invention is in no way thereby limited. In the Examples, acrolein conversion, acrylic acid selectivity and acrylic acid yield are defined by the following equations.

Acrolein conversion (mol %)=(mol number of reacted acrolein/ mol number of supplied acrolein)×100

Acrylic acid selectivity (mol %)=(mol number of formed acrylic acid/mol number of reacted acrolein)×100

Acrylic acid yield (mol %)×(mol number of formed acrylic acid/ mol number of supplied acrolein)×100

Example 1

Into 4000 ml of water, 676 g ammonium molybdate, 149.3 g of ammonium metavanadate and 215.4 g of ammonium paratungstate were dissolved under heating and stirring. Separately, 154.2 g of copper nitrate and 16.1 g of potassium nitrate were dissolved in 200 ml of water under heating and stirring. Thus formed two aqueous solutions were mixed and put into a porcelain evaporator on a hot water bath and stirred with 2500 g of silica-alumina carrier of 5 mm in diameter until the whole system was evaporated to dry solid and the catalytic components were supported on the carrier, followed by a heat treatment in open air at 400° C. for 6 hours. Thus catalyst (1) was obtained, whose metallic elementary composition excepting oxygen was as follows:

$$Mo_{12}V_4W_{2.5}Cu_2K_{0.5}.$$

Catalyst (2) was prepared in the identical manner with preparation of above catalyst (1), except that no potassium nitrate was used. The metallic elementary composition of catalyst (2) excepting oxygen was as follows:

$$Mo_{12}V_4W_{2.5}Cu_2.$$

The activity levels of catalysts (1) and (2) were different As is clear from the results of later appearing Comparative Examples 1 and 2, catalyst (2) had higher activity than catalyst (1).

Stainless steel reaction tubes of 25 mm in inner diameter each which had been heated with molten nitric acid salt, were filled with these catalysts: starting from the gas-inlet side, catalyst (1) was filled to a layer length of 1000 mm, and then catalyst (2) was filled to a layer length of 2000 mm. A reactant gas having the following composition was introduced into the reactor at a space velocity (SV) of 2000 hr$^{-1}$ to be reacted:

| | |
|---|---|
| acrolein | 6 vol. % |
| air | 30 vol. % |
| steam | 40 vol. % |
| inert gases such as nitrogen | 24 vol. % |

The result was as shown in Table 1.

Comparative Example 1

The oxidation reaction of Example 1 was repeated except that catalyst (2) was not used but catalyst (1) alone was filled to a layer length of 3000 mm. The result was as shown in Table 1.

Comparative Example 2

The oxidation reaction of Example 1 was repeated except that catalyst (1) was not used but catalyst (2) alone was filled to a layer length of 3000 mm. The result was as shown in Table 1.

From the results as given in Table 1, it is understood that catalyst (1) has very low activity and that catalyst (2) has high activity but low acrylic acid selectivity, both giving low acrylic acid yields. By contrast, use of the catalyst system in which these catalysts (1) and (2) were combined according to the present invention gave high acrylic acid yield.

Example 2

Into 4000 ml of water, 676 g of ammonium molybdate, 186.6 g of ammonium metavanadate and 129.3 g of ammonium paratungstate were dissolved under heating and stirring. Separately, 154.2 g of copper nitrate, 13.5 g of strontium nitrate and 12.4 g of cesium nitrate were dissolved in 200 ml of water under heating and stirring. The two aqueous solutions were mixed and further 109.8 g of cerium oxide was added thereto, followed by further heating and stirring until the whole system was evaporated to dry solid. The blocks of said solid were further dried in a dryer at 120° C. for 5 hours and pulverized to about 100 mesh in size, to provide a powder. Into a centrifugal flow-coater steatite carrier of 5 mm in diameter was fed and subsequently the above powder was thrown into the flow-coater together with distilled water serving as a binder, through hot air stream of 90° C., to have the carrier carry the catalytic component. The carrier-supported catalyst was heat-treated in air at 400° C. for 6 hours, to provide catalyst (3). The metallic elementary composition of this catalyst excepting oxygen was as follows:

$$Mo_{12}V_5W_{1.5}Cu_2Sr_{0.2}Ce_2Cs_{0.2}.$$

Catalyst (4) was prepared in the identical manner with the preparation of above catalyst (3), except that no cesium nitrate was used. The metallic elementary composition of this catalyst excepting oxygen was as follows:

$$Mo_{12}V_5W_{1.5}Cu_2Sr_{0.2}Ce_2.$$

The oxidation reaction of Example 1 was repeated except that catalyst (3) was used to fill each of the reaction tubes from the gas-inlet side thereof to a layer length of 800 mm, and catalyst (4), to fill the gas-outlet side to a layer length of 2200 mm. The result was as shown in Table 1.

Comparative Example 3

The oxidation reaction of Example 2 was repeated except that catalyst (4) was not used but catalyst (3) alone was filled to a layer length of 3000 mm. The result was as shown in Table 1.

Comparative Example 4

The oxidation reaction of Example 2 was repeated except that catalyst (3) was not used but catalyst (4) alone was filled to a layer length of 3000 mm. The result was as shown in Table 1.

Example 3

Into 4000 ml of water, 676 g ammonium molybdate, 224 g of ammonium metavanadate and 103.4 g of ammonium paratungstate were dissolved under heating and stirring. Separately, 231.3 g of copper nitrate and 24.9 g of cesium nitrate were dissolved in 200 ml of water under heating and stirring. The two resultant aqueous solutions were mixed, and further 76.5 g of titanium oxide and 46.5 g of antimony trioxide were added to the mixture, followed by further heating and stirring for evaporating the system to dry solid. Blocks of the solid were further dried at 120° C. for 5 hours in a dryer and pulverized to about 100 mesh in size, to provide a powder. The powder was shaped into rings of each 6 mm in outer diameter, 2 mm in inner diameter and 6 mm in height with a tabletting machine, and heat-treated at 400° C. for 6 hours in air to provide catalyst (5). The metallic elementary composition of this catalyst excepting oxygen was as follows:

$$Mo_{12}V_6W_{1.2}Cu_3Sb_1Ti_3Cs_{0.4}.$$

Catalyst (6) was prepared in the identical manner with the preparation of above catalyst (5), except that 24.9 g of the cesium nitrate was replaced with 12.9 g of potassium nitrate.

Catalyst (7) was prepared in the identical manner with the preparation of above catalyst (5), except that no cesium nitrate was used. Furthermore, catalyst (8) was prepared in the identical manner with the preparation of catalyst (5), except that the amount of cesium nitrate was varied. The metallic elementary compositions excepting oxygen of catalysts (6), (7) and (8) were as follows:

$Mo_{12}V_6W_{1.2}Cu_3Sb_1Ti_3K_{0.4}$.  catalysts (6)

$Mo_{12}V_6W_{1.2}Cu_3Sb_1Ti_3$.  catalysts (7)

$Mo_{12}V_6W_{1.2}Cu_3Sb_1Ti_3Cs_{0.2}$.  catalysts (8)

Reaction tubes in the same reactor as the one used in Example 1 were charged with catalyst (5), catalyst (6) and catalyst (7) by the order stated, from the gas-inlet side toward the gas-outlet side, to a layer lengths of 800 mm, 800 mm and 1400 mm, respectively, and the reactant gas having the following composition was introduced into the reactor at a space velocity (SV) of 2000 $hr^{-1}$ to carry out the oxidation reaction:

| acrolein | 7 vol. % |
|---|---|
| air | 35 vol. % |
| steam | 10 vol. % |
| inert gases such as nitrogen | 48 vol. % |

The result was as shown in Table 1.

Comparative Example 5

The oxidation reaction of Example 3 was repeated except that catalyst (5) alone was used instead of the combined use of catalysts (5), (6) and (7), which was filled to a layer length of 3000 mm. The result was as shown in Table 1.

Comparative Example 6

The oxidation reaction of Example 3 was attempted, the only change from Example 3 being that catalyst (6) alone was filled in the reaction tubes to a layer length of 3000 mm, instead of the combined use of catalysts (5), (6) and (7). Whereas, the temperature at the hot spot of the catalyst layer exceeded 360° C. and the reaction was suspended. After dropping the reaction temperature to 240° C., the reaction was resumed. The result was as shown in Table 1.

Comparative Example 7

The oxidation reaction of Example 3 was attempted, the only change from Example 3 being that catalyst (7) alone was filled in the reaction tubes to a layer length of 3000 mm, instead of the combined use of catalysts (5), (6) and (7). Although the reaction temperature was dropped to 240° C., still the temperature at the hot spot in the catalyst layer exceeded 360° C. and tended to rise more, and the reaction was stopped.

Example 4

The oxidation reaction of Example 3 was repeated except that catalyst (6) was replaced with catalyst (8). The result was as shown in Table 1.

Comparative Example 8

The oxidation reaction of Example 3 was attempted, the, only change from Example 3 being that catalyst (8) alone was filled in the reaction tubes to a layer length of 3000 mm, instead of the combined use of catalysts (5), (6) and (7). Whereas, the temperature at the hot spot of the catalyst layer exceeded 360° C. and tended to rise more, and the reaction was suspended. After dropping the reaction temperature to 240° C., the reaction was resumed. The result was as shown in Table 1.

TABLE 1

| | Catalyst-filling (Gas-inlet side → (Gas-outlet side) | Reaction Temp. (° C.) | Hot Spot Temp. (° C.) | Acrolein Conversion (mol %) | Acrylic Acid Yield (mol %) | Acrylic Acid Selectivity (mol %) |
|---|---|---|---|---|---|---|
| Example 1 | Catalyst (1)/Catalyst (2) | 250 | 315 | 98.9 | 93.8 | 94.8 |
| Comparative Example 1 | Catalyst (1) | 250 | 317 | 92.6 | 89.0 | 96.1 |
| Comparative Example 2 | Catalyst (2) | 250 | 328 | 99.4 | 91.1 | 91.7 |
| Example 2 | Catalyst (3)/Catalyst (4) | 245 | 319 | 99.3 | 94.5 | 95.2 |
| Comparative Example 3 | Catalyst (3) | 245 | 317 | 94.4 | 90.4 | 95.8 |
| Comparative Example 4 | Catalyst (4) | 245 | 344 | 99.8 | 89.8 | 90.0 |
| Example 3 | Catalyst (5)/Catalyst (6)/Catalyst (7) | 245 | 321 | 99.2 | 92.9 | 93.6 |
| Comparative Example 5 | Catalyst (5) | 245 | 321 | 93.6 | 89.5 | 95.6 |
| Comparative Example 6 | Catalyst (6) | 245 240 | 336 | reaction suspended 98.1 91.1 92.9 | | |
| Comparative Example 7 | Catalyst (7) | 245 240 | | reaction suspended reaction stopped | | |
| Example 4 | Catalyst (5)/Catalyst (8)/Catalyst (7)/ | 245 | 322 | 99.5 | 92.4 | 92.9 |
| Comparative Example 8 | Catalyst (8) | 245 240 | 341 | reaction suspended 98.5 90.6 92.0 | | |

What is claimed is:

1. A process for producing acrylic acid by vapor-phase catalytic oxidation of acrolein or an acrolein-containing gas with molecular oxygen or a molecular oxygen-containing gas using a catalyst-filled fixed bed shell-and-tube reactor, which process is characterized by providing plural reaction zones in each of the reaction tubes in said fixed bed shell-and-tube reactor, by dividing inside of each tube in the axial direction thereof and filling the plural reaction zones with plural catalysts of different activity levels in such a manner that the activity level rises from the gas-inlet side of each reaction tube toward the gas-outlet side thereof, wherein the catalysts are oxides or complex oxides having the metallic elementary composition represented by the following general formula (I):

$$Mo_aV_bW_cCu_dA_eQ_fR_gD_hO_i \qquad (I)$$

wherein Mo is molybdenum; V is vanadium; W is tungsten; Cu is copper; A is an element selected from the group consisting of zirconium, titanium and cerium; Q is an element selected from the group consisting of magnesium, calcium, strontium and barium;

R is an element selected from the group consisting of niobium, antimony, tin, tellurium, phosphorous, cobalt, nickel, chromium, manganese, zinc and bismuth; D is an element selected from alkali metals; and O is oxygen; and a, b, c, d, e, f, g, h and i represent atomic ratios of Mo, V, W, Cu, A, Q, R, D and O, respectively, in which where a is 12, $1 \leq b \leq 14$, $0 < c \leq 12$, $0 < d \leq 6$, $0 \leq e \leq 10$, $0 \leq f \leq 3$, $0 \leq g \leq 10$ and $0 < h \leq 5$, and i is a numerical value determined by degree of oxidation of each of the elements.

2. The process according to claim 1, in which plural catalysts which are prepared with the kind and/or amount of the D-group element or elements in the general formula (I) varied and which have different activity levels are filled in the plural reaction zones in such a manner that the activity level rises from the gas-inlet side toward the gas-outlet side.

3. The process according to claim 1 or 2, in which the number of reaction zones is 2 or 3.

* * * * *